United States Patent
Melker et al.

(10) Patent No.: US 10,674,923 B2
(45) Date of Patent: Jun. 9, 2020

(54) DEVICES AND METHODS FOR MONITORING DIRECTIONAL BLOOD FLOW AND PULSE WAVE VELOCITY WITH PHOTOPLETHYSMOGRAPHY

(71) Applicants: University of Florida Research Foundation, Inc., Gainesville, FL (US); Xhale, Inc., Gainesville, FL (US)

(72) Inventors: Richard J. Melker, Gainesville, FL (US); Sean Cohen, Gainesville, FL (US)

(73) Assignees: UNIVERSITY OF FLORIDA RESEARCH FOUNDATION, INCORPORATED, Gainesville, FL (US); XHALE ASSURANCE, INC., Gainesville, FL (US)

(*) Notice: Subject to any disclaimer, the term of this patent is extended or adjusted under 35 U.S.C. 154(b) by 1112 days.

(21) Appl. No.: 14/775,005

(22) PCT Filed: Mar. 13, 2014

(86) PCT No.: PCT/US2014/026359
§ 371 (c)(1),
(2) Date: Sep. 11, 2015

(87) PCT Pub. No.: WO2014/168718
PCT Pub. Date: Oct. 16, 2014

(65) Prior Publication Data
US 2016/0022157 A1    Jan. 28, 2016

Related U.S. Application Data

(60) Provisional application No. 61/798,363, filed on Mar. 15, 2013.

(51) Int. Cl.
*A61B 5/00* (2006.01)
*A61B 5/026* (2006.01)
(Continued)

(52) U.S. Cl.
CPC ............ *A61B 5/0261* (2013.01); *A61B 5/021* (2013.01); *A61B 5/0295* (2013.01);
(Continued)

(58) Field of Classification Search
None
See application file for complete search history.

(56) References Cited

U.S. PATENT DOCUMENTS

2008/0039731 A1    2/2008 McCombie et al.
2009/0227881 A1    9/2009 Reichman et al.
(Continued)

FOREIGN PATENT DOCUMENTS

EP        2967366 A1     1/2016
WO   2010082748 A2     7/2010
(Continued)

OTHER PUBLICATIONS

Foreign search report for CA 2,897,943, dated Oct. 5, 2016.
(Continued)

*Primary Examiner* — Joel Lamprecht
(74) *Attorney, Agent, or Firm* — Thomas | Horstemeyer, LLP

(57) ABSTRACT

Provided according to embodiments of the invention are methods of monitoring the direction of blood flow that include processing with a computer photoplethysmography (PPG) signal streams from a sensor array on a body site of the individual to determine the direction and/or velocity of the blood flow at the body site of the individual. In some embodiments, direction of the blood flow at the body site is determined by the phase difference between at least three PPG signal streams from the sensor array, wherein the at least three PPG signal streams are generated from emissions of the at least three emitters.

14 Claims, 6 Drawing Sheets

(51) Int. Cl.
  *A61B 5/0295* (2006.01)
  *A61B 5/021* (2006.01)
  *A61B 5/08* (2006.01)
  *A61B 5/087* (2006.01)

(52) U.S. Cl.
  CPC ........ *A61B 5/02108* (2013.01); *A61B 5/4064* (2013.01); *A61B 5/6819* (2013.01); *A61B 5/7278* (2013.01); *A61B 5/082* (2013.01); *A61B 5/087* (2013.01); *A61B 2562/043* (2013.01); *A61B 2562/046* (2013.01); *A61B 2562/164* (2013.01)

(56) References Cited

U.S. PATENT DOCUMENTS

| | | |
|---|---|---|
| 2010/0113948 A1 | 5/2010 | Yang et al. |
| 2010/0168589 A1 | 7/2010 | Banet et al. |
| 2012/0053469 A1* | 3/2012 | Melker .............. A61B 5/02007 600/479 |
| 2013/0041268 A1 | 2/2013 | Rimoldi et al. |
| 2014/0005557 A1 | 1/2014 | Rich et al. |
| 2016/0022157 A1 | 1/2016 | Melker et al. |

FOREIGN PATENT DOCUMENTS

| | | |
|---|---|---|
| WO | 2010082748 A3 | 7/2010 |
| WO | 2011103102 A1 | 8/2011 |
| WO | WO2014168718 A1 | 10/2014 |

OTHER PUBLICATIONS

Foreign search report for CA 2,897,943, dated Jul. 27, 2017.
Saban Y, Amodeo C, Bouaziz D, Polselli R. Nasal Arterial Vasculature: Medical and Surgical Applications. Arch Facial Plast Surg. 2012:14(6):429-436. doi:10.1001/archfacial.2012.202.
Bhimji, Shabir and Kupferschmid, John. "Pulmonary Artery Banding." http://emedicine.medscape.com/article/905353-overview#aw2aab6b2b1aa (2014).
International Search Report and Written Opinion for PCT/US2014/026359 dated Jul. 24, 2014.
Brooks, et al: "A Review of Position Tracking Methods"; 1st International Conference on Sensing Technology Nov. 21-23, 2005 Palmerston North, New Zealand.
Chen, et al: "Determining RF Angle of Arrival Using COTS Antenna Arrays: A Field Evaluation"; MILCOM 2012—2012 IEEE Military Communications Conference.

\* cited by examiner

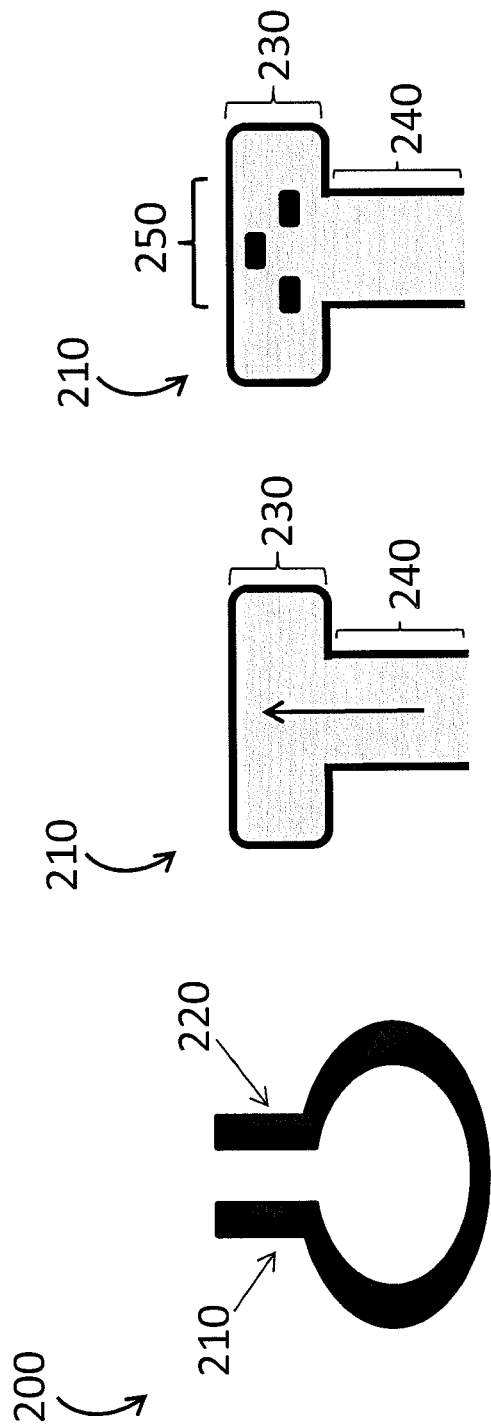

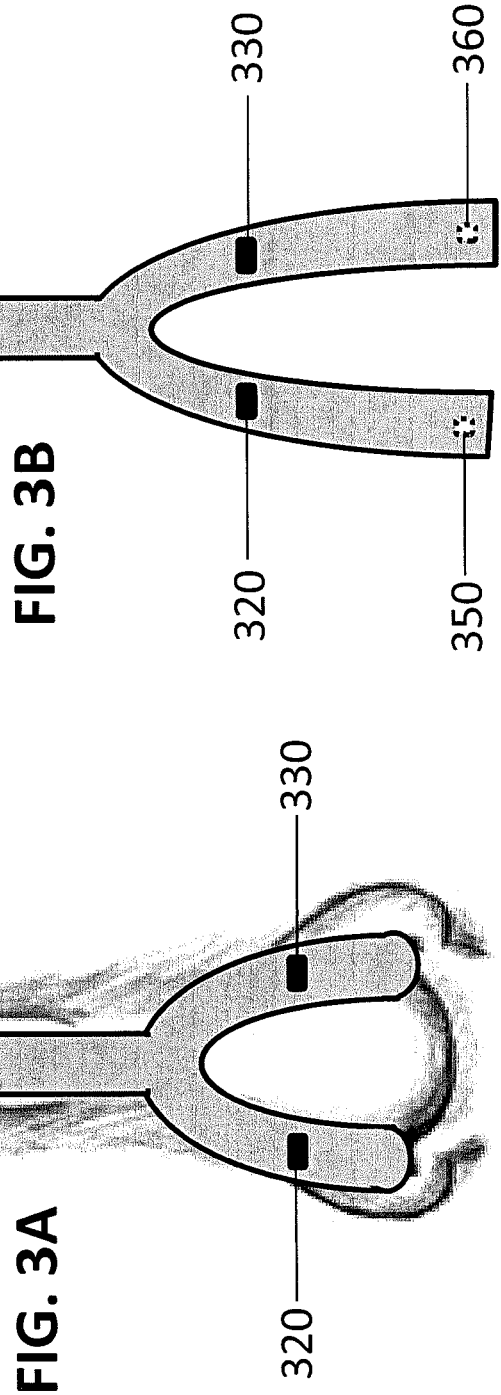

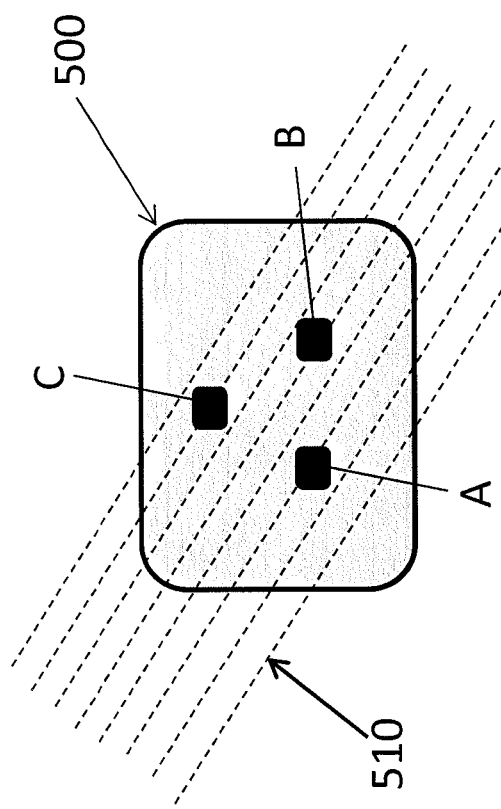
FIG. 5A
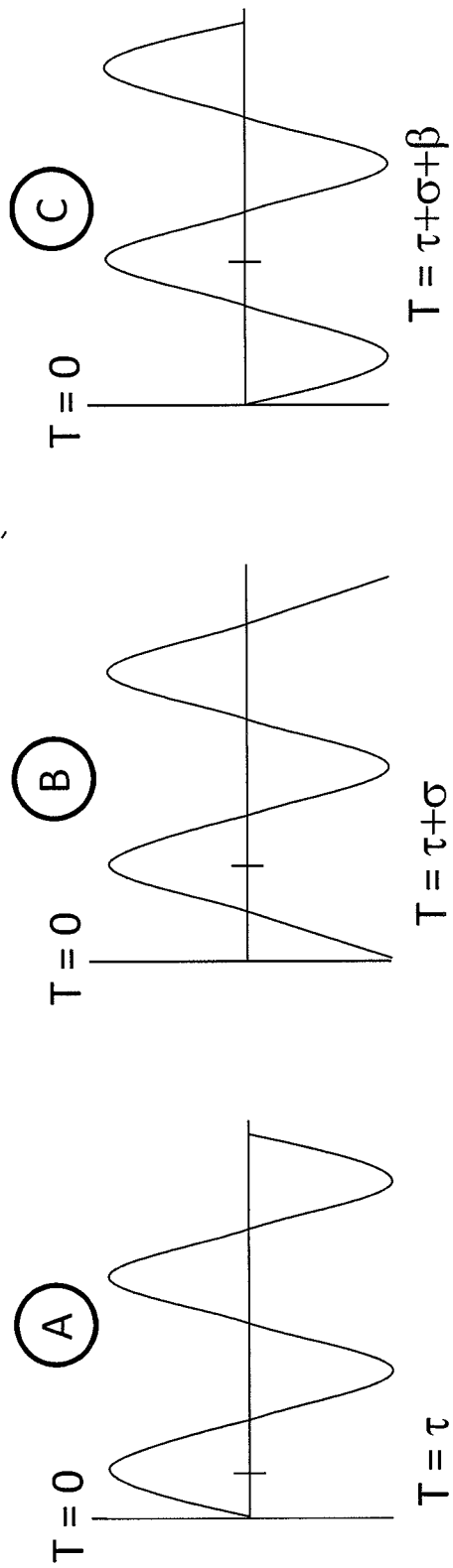
FIG. 5B
FIG. 5C
FIG. 5D

DEVICES AND METHODS FOR MONITORING DIRECTIONAL BLOOD FLOW AND PULSE WAVE VELOCITY WITH PHOTOPLETHYSMOGRAPHY

CROSS-REFERENCE TO RELATED APPLICATIONS

This application is the 35 U.S.C. § 371 national stage of, and claims priority to and the benefit of, PCT application PCT/US2014/026359, filed Mar. 13, 2014, which claims priority to and the benefit of U.S. Application No. 61/798,363 filed Mar. 15, 2013, the disclosure of each which is herein incorporated by reference in their entirety.

FIELD OF THE INVENTION

The present invention relates to biological sensors, and in particular, to photoplethysmography sensors. The present invention also relates to systems and devices for use with photoplethysmography sensors, as well as methods of using photoplethysmography sensors.

BACKGROUND OF THE INVENTION

Photoplethysmography, or "PPG", is an optical technique for detecting blood volume changes in a tissue. In this technique, one or more emitters are used to direct light at a tissue and one or more detectors are used to detect the light that is transmitted through the tissue ("transmissive PPG") or reflected by the tissue ("reflectance PPG"). The volume of blood, or perfusion, of the tissue affects the amount of light that is transmitted or reflected. Thus, the PPG signal may vary with changes in the perfusion of the tissue.

The blood volume in a tissue changes with each heartbeat, and so the PPG signal also varies with each heartbeat. Traditionally, this component of the PPG signal is referred to as the "AC component" of the signal, and is also often referred to as the "pulsatile component." Blood volume is also affected by other physiological processes in the body, including respiration, venous blood volume, sympathetic and parasympathetic tone and certain pathologies. The changes in the PPG signal due to these and other physiological processes, along with changes in the PPG signal due to noise caused by non-physiological processes such as ambient light and bodily movement, have traditionally been referred to collectively as the "DC component."

The isolated AC and DC component signals, as well as the combined PPG signal, in some cases, have been used to monitor a number of physiological parameters, including blood oxygen saturation, perfusion, respiration, blood volume, magnitude of blood flow and the like. However, there remains significant untapped potential in using PPG to monitor physiological processes.

BRIEF DESCRIPTION OF THE DRAWINGS

The following drawings are provided to illustrate various aspects of the present inventive concept and are not intended to limit the scope of the present invention unless specified herein.

FIG. 1A is an external view and FIG. 1B is a laid open view of the internal face of the sensor.

FIGS. 2A-2C provide different views of a 2D clip sensor according to an embodiment of the invention. FIG. 2A provides a side view of the clip sensor, FIG. 2B provides a view of an end portion of the clip sensor, and FIG. 2C provides a view of the internal face and sensor array for this embodiment.

FIGS. 3A and 3B show two views of a 3D nose and forehead directional sensor. FIG. 3A shows the sensor as secured onto an individual and FIG. 3B shows the sensor before the detectors are inserted into the nostrils.

FIGS. 5A-5D provide schematics illustrating how direction and velocity of blood flow are determined by the geometry of a sensor array according to some embodiments of the invention.

DETAILED DESCRIPTION OF EMBODIMENTS OF THE INVENTION

Figure 1B:
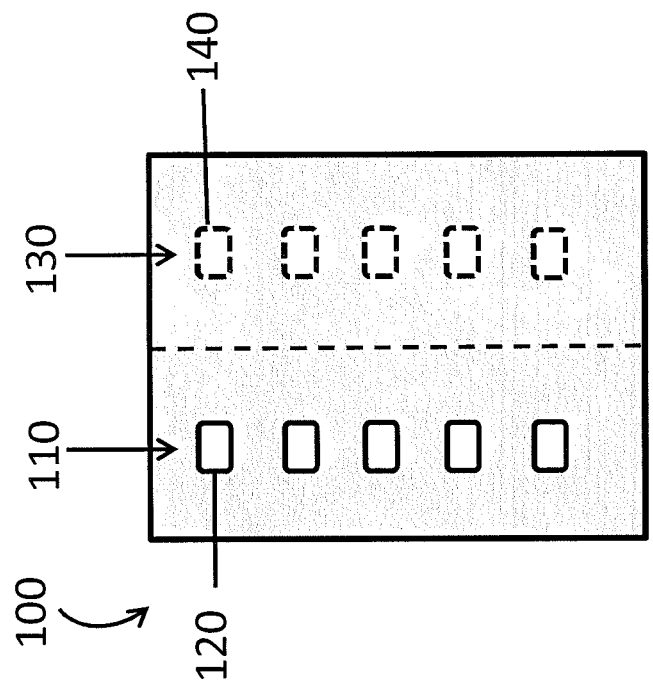
FIGS. 1A and 1B show two different views of a one dimensional cuff PPG sensor according to an embodiment of the invention.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "on" or "adjacent" to another element, it can be directly on or directly adjacent to the other element or intervening elements may also be present. In contrast, when an element is referred to as being "directly on" or "directly adjacent" to another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers refer to like elements throughout the specification.

It will be understood that, although the terms first, second, etc. may be used herein to describe various elements, these elements should not be limited by these terms. These terms are only used to distinguish one element from another. Thus, a first element discussed below could be termed a second element without departing from the teachings of the present invention.

Embodiments of the present invention are described herein with reference to schematic illustrations of idealized embodiments of the present invention. As such, variations from the shapes of the illustrations as a result, for example, of manufacturing techniques and/or tolerances, are to be expected.

Provided according to embodiments of the present invention are devices, systems and methods for monitoring directional blood flow and/or blood velocity, optionally along with other parameters. Such devices, systems and methods use a sensor array to obtain two or more (and typically three or more) photoplethysmography (PPG) signal streams from a single body site of an individual. By analyzing the differences (e.g., the change in phase) between multiple PPG signal streams at one body site, information regarding the direction of blood flow and/or the speed of the blood flow (e.g., pulse transit time or pulse wave velocity) can be determined. Other parameters, such as blood pressure, may also be calculated.

PPG Devices Including Sensor Arrays

Provided according to some embodiments of the present invention are novel PPG sensors. Such sensors may include an array of emitters and/or an array of detectors, and either of which (or both together) may be referred to herein as a "sensor array." Generally, a sensor array includes at least three emitters and/or at least three detectors, and various combinations may be used. For example, in some cases, at least three emitters may be used with one detector. In some cases, the sensor includes at least three emitters and two detectors, and in some cases, the sensor includes at least three emitters and at least three detectors. Inversely, in some embodiments, the PPG sensor may include one emitter and three detectors. Additionally, in some embodiments, the PPG sensor may include two emitters and three detectors. There is no limitation on the number of emitters and/or detectors that are included in a sensor array. Thus, for example, a PPG sensor may include 4, 5, 6, 7, 8, 9, 10 or more emitters and/or detectors.

In some cases, a sensor array may only have 1 emitter (e.g., an emitter pair with red and IR emitters) and 2 detectors, or 2 emitters (each with red and IR emitters) and 1 detector, but in many cases, three or more emitters and/or detectors are needed to obtain the desired information, for example, in the determination of the two or three dimensional direction of blood flow.

Many different configurations of the sensor array are possible, and any suitable configuration may be used. Furthermore, the sensor array may be a linear, 2D or 3D array. In some cases, the configuration of the array may be optimized for a particular use or body site. Examples include T-shaped, circumferential and radial. Particular examples of arrays that may be used according to particular embodiments will now be described.

Figure 1A:
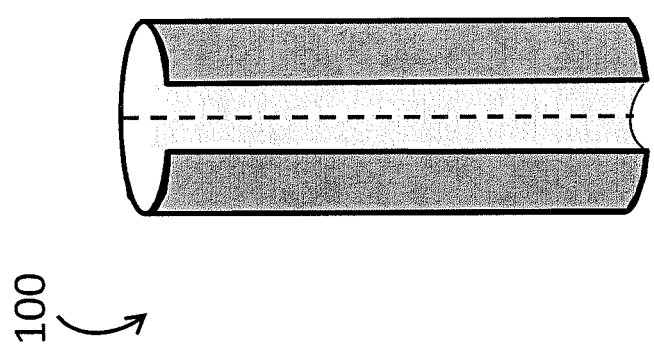

FIGS. 1A and 1B provides two views of a linear sensor array. In this case, the linear array is included on a "cuff" or cylindrical sensor body, and so may be useful for fitting, e.g., to an arm, wrist, leg, digit, an internal organ or tissue, or an arterio-venous shunt. FIG. 1A provides an external view of a cuff sensor 100, and FIG. 1B provides a view of a particular embodiment of a cuff sensor 100 that is opened and laid flat. As shown in FIG. 1B, one side of the cuff sensor 100 may have an emitter array 110, which, in this embodiment, includes a linear emitter array 110 of five individual LED components 120. On the other side of the cuff sensor 100 is a detector array 130 that includes a linear array of five photodetectors 140. When the cuff sensor 100 is closed around the body site, the emitter array 110 and the detector array 130 may be configured so that each photodetector 140 detects light from at least one of the LED components 120.

In some cases, the emitter array 110 and detector array 130 are configured such that the sensor uses transmissive PPG and in some cases the emitter array 110 and detector array 130 are configured such that the sensor uses reflectance PPG. The emitter array 110 and the detector array 130 may thus, in some cases, be situated more closely together. Further, as described above, in some cases, the number of detectors 140 may be different than the number of emitters 120. For example, one detector 140 may be used to detect radiation from two or more emitters 120.

FIGS. 2A-2C show a clip PPG sensor that includes a 2D sensor array. FIG. 2A provides a side view of the sensor 200, which may be used, for example, at the nose (alar, septum, columella) or ear, and the like. The clip sensor 200 includes two end portions 210 and 220 that may grasp to secure to a tissue site. FIG. 2B shows an end on view of the end portion 210 of the sensor in FIG. 2A, whereby the upper part 230 of the end portion 210 is wider than the lower part 240 of the clip body. FIG. 2C shows an internal face of the first end portion 210 with a 2D emitter array 250. The other internal face (not shown) of the clip sensor 200 may, for example, have one or more detectors configured to detect light from the 2D emitter array 250. The term "2D sensor array" refers to the fact that the three emitters are all in the same plane, however, if the emitters are not in the same spatial plane, the sensor 200 may be considered to have a 3D sensor array.

FIGS. 3A and 3B show a PPG sensor 300 having a 3D sensor array configured with an emitter on the forehead 310 and emitters on the nose 320, 330. The PPG sensor 300 also includes a reflectance detector 340. In FIG. 3A, the detectors for the emitters on the nose 320, 330, are inside the nose and so are not shown. FIG. 3B shows the PPG sensor 300 from FIG. 3A prior to the insertion of photodetectors 350, 360 into the nose. The detectors 350, 360 are configured to detect light from the emitters on the nose 320, 330, respectively. In this embodiment, the broken line of the detectors 350, 360 signifies that the detectors 350, 360 are on the opposite face of the sensor. While FIGS. 3A and 3B show a PPG sensor 300 having three pairs of emitters and detectors, such a PPG sensor 300 may have additional emitters and/or detectors at the same locations or at different locations. The term "3D sensor array" refers to the fact that the sensors are not all in the same spatial plane.

As used herein, the term "emitter" refers to an electronic component that emits light. As used herein, the term "light" is used generically to refer to electromagnetic radiation, and so the term includes, for example, visible, infrared and ultraviolet radiation. Any suitable type of emitter may be used, but in some embodiments, the emitter is a light-emitting diode (LED). In particular embodiments, an emitter emits light at a particular wavelength. In some cases, a single emitter may emit light at a first wavelength and a second wavelength. As used herein, the "detector" is configured to detect light from an emitter, and this detected light generates a PPG signal. Any suitable photodetector may be used. However, examples of photodetectors include photodiodes, photoresistors, phototransistors, light to digital converters, and the like.

In some embodiments of the invention, the PPG sensor includes a sensor body and the sensor array is therein or thereon. The sensor body may provide support for the sensor array and facilitate the securing of the sensor onto a body site. The term "secure" means to attach sufficiently to the tissue site to allow for a suitable PPG signal to be generated. In some cases, the sensor body is configured to secure onto a tissue site such that no additional support is necessary to allow for a suitable PPG signal to be reliably generated.

However, in some cases, the sensor body may be secured with the aid of an external support, for example, an additional structural support, a wire or cord, or an adhesive product such as tape. Such supports may be desirable to stabilize the sensor to prevent against signal loss, for example, due to the patient's movement, or due to movement (e.g., jostling, pulling, pushing) of the sensor or a cable attached thereto.

A sensor body may be formed of any suitable material, including but not limited to, metals, polymers, polymer blends, and combinations thereof. The type of metal, polymer or polymer blend used depends on the type of PPG sensor and its intended use. As such, many thermoplastic and thermoset polymers may be suitable for use in the sensor body. However, in particular embodiments, the sensor body includes polycarbonate, acetal, nylon, polyester, or a combination thereof. Many metals may also be suitable for use in the sensor body, and in some embodiments, malleable metals, such as aluminum or nitinol, may be desirable. In particular embodiments, the sensor body is a molded article, such as a molded polymer article or a molded metallic article. In some embodiments, the material of the sensor body and/or clip is highly opaque and non-tranmissive of light in the visible and IR spectrums to prevent the light from an emitter from reaching the detector without first passing through tissue at the measurement site.

The sensor body may be composed of smaller pieces, which are assembled to form the sensor body, but in some embodiments, the sensor body is a single molded article. The use of a single molded article eliminates the need for assembly of the sensor body, and so may increase manufacturing efficiency and/or decrease manufacturing costs. In some embodiments, the sensor body may be flexible and/or malleable. Any suitable method of making the sensor body may be used. In some embodiments, the sensor body is manufactured by inserting a fluid monomer, polymer and/or polymer blend into a mold, and solidifying the monomer or polymers. For example, a monomer may be polymerized in order to form a solid sensor body. In other embodiments, a melted or softened polymer or polymer blend is inserted into a mold and the temperature of the material is lowered until the polymer material solidifies. Such methods are known to the skilled artisan, and any technique for creating molded polymer articles may be used.

In certain embodiments of the invention, the sensor body is a clip, and so will be referred to herein as a "clip body." The term "clip body" refers to a device that has at least two end portions that grasp and secure to a tissue site. An example of a clip body is shown in FIG. 2A. The clip body may be configured in a number of shapes, including, for example, "U-shaped" or "C-shaped", squared, rounded, pointed, regular or irregular shaped. In particular embodiments, the clip body may be configured to conform a curvature of a particular tissue.

In some cases, there may be additional structural, functional or design elements in or on the sensor/clip body. For example, the sensor/clip body may have additional arms or extensions, and so may have additional end portions. The sensor/clip body may also be configured so that it can retract or extend to facilitate adjustment or placement of the sensor. Other configurations of sensor/clip body and other features, including apertures in the sensor body and elastomeric sleeves, may be used, including those described in U.S. Patent Application Publication No. 2014/0005557, entitled "Photoplethysmography Sensors," incorporated by reference herein in its entirety.

The emitters and detectors of the PPG sensor may be attached or combined with the sensor body in any suitable fashion. However, in some embodiments, a flex circuit in the PPG sensor includes the electronic components. In some cases, the PPG sensor includes a flex circuit without any sensor body support structure, while in other embodiments, the flex circuit is in, on or adjacent to a sensor body in the PPG sensor. While any suitable type of flex circuit may be used, in some embodiments, the flex circuit is a single electrically conductive layer, housed in insulative plastic, which has all of the electronic components on the same side of the circuit. Furthermore, in particular embodiments, the flex circuit includes a moisture protective conformal coating.

Electronic components that provide additional physiological monitoring to the sensor may also be included in the sensor. Examples of physiological monitoring components that may be included on the flex circuit, or otherwise provided to the sensor, include respiration detectors such as thermistors, thermocouples, RTDs, moisture detectors, capnometers, microphones, pressure sensors, including differential flow transducers, nasal airway flow detectors, and vibration detectors. Other physiological monitoring components that may be included in the sensor include ECG leads, oxygen sensors, pH sensors, and sensors for identifying and/or measuring particular compounds in the nasal airflow.

In some embodiments, an electronic component for wireless communication may be included on the sensor. Any suitable wireless communication component may be included on the flex circuit, but in some embodiments, a Bluetooth®, WiFi and/or infrared technology may be used. Such electronic components may communicate with a receiver apparatus so that PPG signals acquired by the sensor may be transmitted wirelessly to a control and/or signal processing unit.

In some embodiments, the electronic components are mounted on the flex circuit, and this may be achieved by any suitable technique, including, for example, via soldering and/or adhesives. The electronic components may also be mounted in any suitable configuration and on any part of the flex circuit. For example, in some cases, an emitter may be mounted on a first end portion of the flex circuit and the detector may be mounted on a second end portion of the flex circuit. Furthermore, in some embodiments, an emitter and a detector may be on the same end portion of the flex circuit, and in some cases, may be adjacent to each other. In some embodiments, the electronic components are "through-hole components" or "chip on board" components, so that the electronic components are not mounted on the surface of the flex circuit but are otherwise incorporated into the flex circuit. It is also to be understood that while the flex circuit is included to introduce electronic components to the sensor, in some embodiments, electronic components may also be present on other portions of the sensor, including the sensor body.

In some embodiments, the flex circuit includes or is attached to a wire or cable for transmitting or communicating signals from the sensor to a computer or other analysis/processing equipment. In some cases, a portion of flex circuit itself may be considered part of the cabling. The flex circuit may also include a connector for coupling the flex circuit to a wire, cable or another electronic device. Any suitable wire, cable or other electrical connector may be used as the connector. In other embodiments of the invention, the PPG signals may be transmitted wirelessly, and so no wire or cabling is needed, and thus, the flex circuit may not include any cables or connectors.

According to some embodiments of the invention, the PPG sensor is partially or completely disposable. As such, the sensor may be used for a single use or for more than one use, for example, 2-10 uses, including 2, 3, 4 or 5 uses. In such cases, the sensor may be formed from a sufficiently inexpensive material that also meets safety and performance standards. The disposability of the sensor may be advantageous in some cases because it may decrease or eliminate the need for cleaning and disinfection, which may, in turn, improve the ease of use for medical personnel.

According to some embodiments of the present invention, the PPG sensor is configured to secure to the nasal alar region of the nose, which may also be referred to herein as the "nasal alar", "alar" or "ala", and may also be referred to elsewhere as the nasal "wing". Further information regarding the nasal alar region and sensors designed therefore can be found in U.S. Patent Application Publication No. 2014/0005557, entitled "Photoplethysmography Sensors," incorporated by reference herein.

The nasal sensors, according to particular embodiments, may also include a nasal cannula for delivery of breathing gases, such as oxygen or oxygen-enriched air. The nasal cannula may be incorporated into the nasal sensor in a number of different ways. For example, in some embodiments, the nasal cannula may be affixed to the outside (or inside) of the sensor so that it is inserted into the nostril with the end portion of the sensor that secures inside the nasal cavity. As another example, in some cases, a sensor body may have an aperture defined therein, so that the cannula may run through the sensor body.

Any suitable method of making the PPG sensors described herein may be used. Known methods of making such sensors may be used, including, for example, those described in U.S. Patent Application Publication No. 2014/0005557, entitled "Photoplethysmography Sensors," incorporated by reference herein. A flex circuit may be purchased in a condition suitable for inclusion in the PPG sensors described herein, but in some cases, the flex circuit is first prepared by mounting the desired electronic components on the appropriate sections of the flex circuit. Surface mounting of electronic components onto flex circuits is known in the art, and so any suitable technique, including soldering or adhesives, may be used. The flex circuit may also be further prepared by introducing a connector onto the flex circuit, such as, for example, soldering pads on the flex circuit for use as a connector. In order to have the electronic components in the proper location for joining with the sensor body, the flex circuit may also be folded and secured, such as via an adhesive, in a folded configuration.

Figure 4:
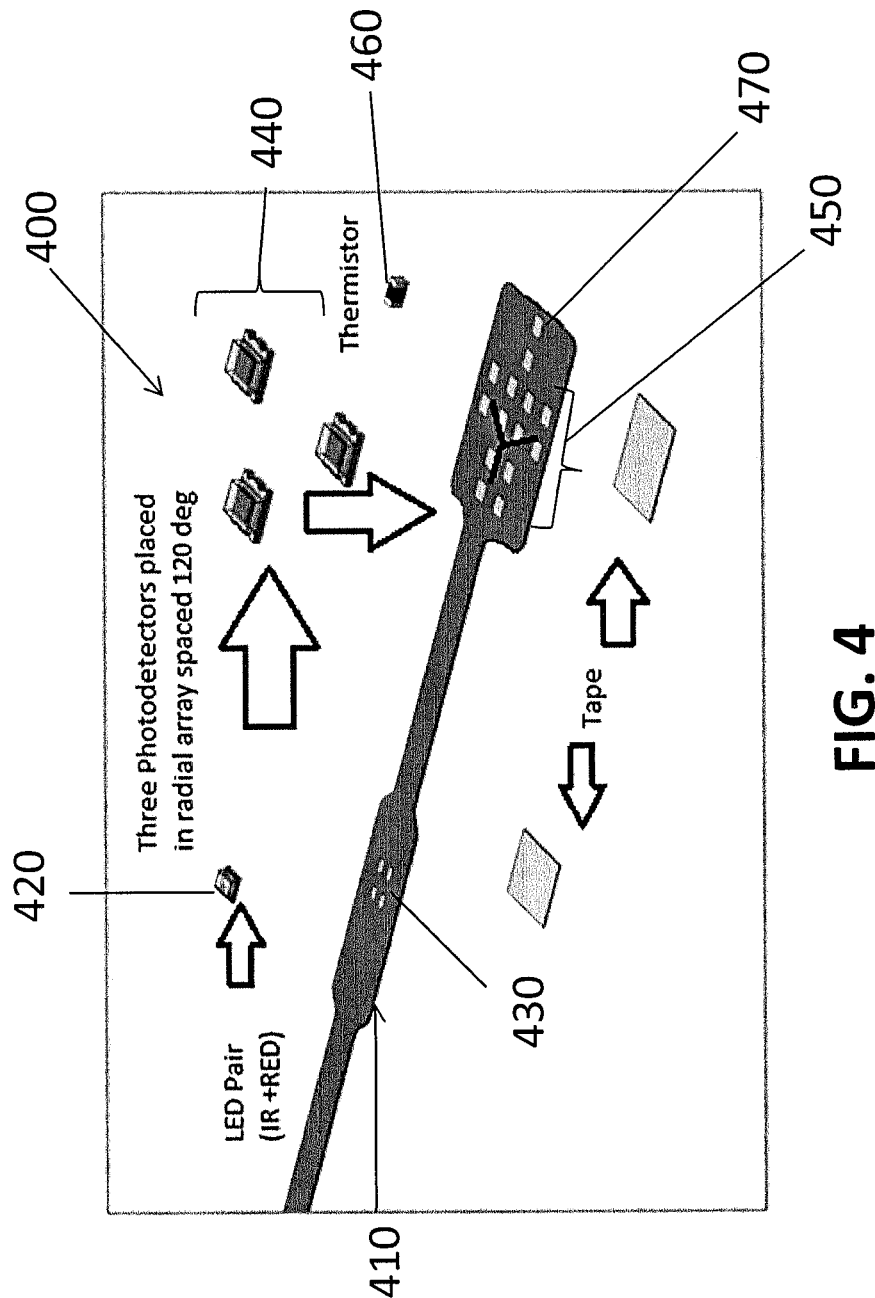
FIG. 4 provides an illustration of a flex circuit and electronic components that may be used to make a sensor array according to an embodiment of the invention.

FIG. 4 shows a method of forming a sensor array 400 on a flex circuit 410 according a particular embodiment of the invention. In this embodiment, an emitter (IR+Red) 420 is soldered to a first set of pins 430. Three detectors 440 are soldered onto a second set of pins 450. In this embodiment, a thermistor 460 is also soldered to a third set of pins 470. Tape may then be used to fold and secure the flex circuit for joining with a sensor body.

Methods and Systems for Monitoring Directional Blood Flow and Blood Velocity

Provided according to some embodiments of the present invention are methods of monitoring directional blood flow and/or velocity of blood flow in an individual. In some embodiments of the invention, two or more (and typically three or more) photoplethysmography (PPG) signal streams from a sensor array on a body site of the individual may be processed using a signal processor/computer to determine the direction and/or velocity of the blood flow at the body site of the individual. In some embodiments, methods provided herein may include: (a) securing a sensor array at a body site of an individual; (b) obtaining at least two PPG signal streams from the sensor array; and (c) analyzing the at least two PPG signal streams to determine the direction and/or velocity of blood flow at the body site.

The term "body site" refers to a localized region of the body for which the direction of the blood flow (or other parameter) is being ascertained. For example, in some cases, the body site may be a single arterial blood vessel. In some cases, the body site is defined as a very small region surrounding a single blood vessel. In other cases, the body site may describe a large external region of the body such as the leg or arm or face. In other cases the body site may be described as a section of internal tissue containing vasculature where the relative magnitude, direction, and speed of flow are of interest. As used herein, the terms "PPG signals" or "PPG signal streams" refer to the raw PPG signal streams, as well as filtered or processed signals, including in some embodiments, the isolated AC and/or isolated DC component signal streams. Both the combined and isolated signal streams may be used in embodiments described herein. As used herein, the term "individual" includes both human and animal subjects.

The sensors may be secured to the patient in any suitable manner. For example, a sensor may be placed onto a subject, the sensor may be physically or electronically connected to a signal processing apparatus, and signals may be generated. In embodiments wherein a wireless sensor is used, no connection of wires or cables may be necessary for use. In some cases, the sensor may be additionally secured by taping the sensor, flex circuit and/or any additional cabling. As described above, this may ensure that the sensor remains in place despite patient movement or jostling of the sensor or cables, for example, by medical personnel.

In some embodiments, the direction of blood flow may be determined by analyzing the phase difference between the two or more signal streams from the sensor array to determine the direction of blood flow. Specifically, the direction of the blood flow may be determined by: (1) determining the phase differences between the at least two PPG signal streams, and (2) using the phase differences and the geometry of the sensor array to determine the direction and/or velocity of the blood flow at the body site. The methods described herein may also be used to determine speed, volume of blood flow, blood pressure, and the like, as will be described in further detail below. Such measurements may also be obtained in combination with other cardiorespiratory parameters such as blood oxygen saturation, pulse, respiratory rate and respiratory effort, which parameters may also be determined using PPG.

The primary basis for obtaining the aforementioned parameters is the fact that the sensor arrays are able to generate multiple PPG signal streams, each signal stream being generated at a defined location relative to the other signal streams. This allows for sampling of blood flow data at different spatial and geometric points in a localized area, which over time can provide information about the direction (and speed, velocity, etc.) the blood is moving at that body site in the individual. Thus, the system first collects waveforms (signal streams) from the sensor array. A computer/signal processor in communication with the sensor array then compares the two, three or more signal streams over time to analyze the phase difference and/or other differences (e.g., amplitude) in the signal streams to assess the relationship between the signals, and ultimately the direction of the blood flow. Any suitable method to calculate such parameters may be used. However, in some embodiments of the invention, the speed and direction of blood flow are determined using "Time Difference of Arrival" (TDoA) and/or "Angle of Arrival" (AoA) calculations from peak detection, zero crossing, or by means of phase difference, whereby the source of flow may be obtained by multilateration or multiangulation analysis of the signals.

In some embodiments, an emitter/detector pair (also referred to herein as a "node") in the sensor array may be sampled synchronously or in sequence depending on the geometry and the desired application. For example, synchronous sampling may be possible in an array having a single central emitter and detectors that are sampled simultaneously. Synchronous sampling may also be possible when multiple emitters are far enough outside the line of sight of a single detector to prevent crosstalk. Sequenced pulsing may be desirable when there is the possibility of neighboring emitters (or those sharing a detector) interfering, as in the linear array or single detector geometries. By sequencing the nodes at sufficiently high frequency, error introduced by the migration of pulsatile blood flow can be reduced.

In a particular sequential pulsing embodiment, as each emitter is pulsed on, the detector will sample the absorption between itself and the emitter. When a first emitter is extinguished and the second emitter is pulsed on at a known distance from the first, the detector again takes a sample of absorption between itself and the second emitter. As the pulsatile flow has not had time to change position significantly, the new absorption sample will have a phase offset relative to its distance from the previous emitter. Similarly, a centrally located detector can be used that is sampled as each emitter in the array is pulsed on. This process can be repeated for each emitter in the array in a "round robin" manner indefinitely providing a constant stream of signals with phase differences relative to the direction of pulsatile flow.

In a particular synchronous pulsing embodiment, a centrally located emitter is pulsed on in sync with the sampling of the detectors. As the peaks and zero crossings of the PPG signal will occur at slightly different times because of the know distance separation of nodes, multilateration or multiangulation can be used to compute the direction of pulsatile flow. Similarly, if the array is constructed with multiple emitters and detectors that are separated by such a distance that the emitter of one node cannot affect the detector of a different node (crosstalk), then all nodes can be sampled synchronously and evaluated as described before.

FIGS. 5 and 6 illustrate in more detail how the geometry of the sensor may be used to calculate blood flow direction and velocity using the sensor arrays described herein. In these embodiments, there are three emitters A, B and C, and a single detector (not shown) in the sensor array 500. The three emitters A, B and C are pulsed in sequence at a sufficiently high rate so that the each emitter is sampling substantially the same blood flow (wherein the blood flow has direction 510) at sites separated by a known distance. The separation of nodes creates a phase shift between recorded PPG signals. This phase shift cause peaks and zero crossing events to happen at slightly different times between the three nodes. This is defined as the Time Difference of Arrival (TDoA). The Angle of Arrival (AoA) may also be calculated with this information.

The direction of blood flow, with respect to a reference direction, may be determined based on the first zero crossing or peak value between the three signals. This is called the leading node. Comparing the exact phase difference between the leading node and remaining two nodes reveals the exact direction of incoming pulsatile flow. If the source direction changes slightly the TDoA between the leading node and the other nodes will necessarily change. If the direction changes considerably, a new leading node is chosen and the process is repeated. In this way, the direction of the flow is calculated and communicated relative to the reference direction established initially. Adding more nodes allows more precise estimation of direction.

For example, in FIG. 5, the flow 510 originates from the bottom left. Emitter A is the leading node in this situation. We define the TDoA between nodes as $\tau$ from T=0 to emitter A, $\sigma$ from emitter A to emitter B, and $\beta$ from emitter B to emitter C. In the case of FIG. 5A, we can set $\sigma=\beta$ because emitter B is located exactly between emitter A and emitter C relative to the incoming direction. In this case, emitter C is defined as the trailing node. FIGS. 5B-5D illustrate the phase shift of the PPG waveforms caused by the separation of the three nodes. In FIG. 5B, the waveform generated by emitter A is shown. In FIG. 5C, the waveform generated by emitter B is shifted by a first phase difference ($\sigma$) and in FIG. 5D, the waveform is shifted additional phase difference ($\beta$), whereby the phase difference between the waveform generated by emitter A and the waveform generated by emitter C is $\sigma+\beta$.

Figure 6A:
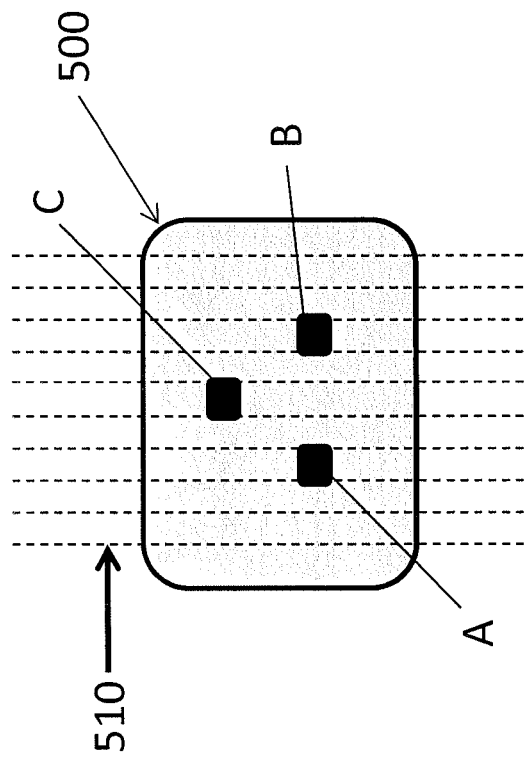
FIGS. 6A-6D provide schematics illustrating how direction and velocity of blood flow are determined by the geometry of a sensor array according to some embodiments of the invention.
Figure 6D:
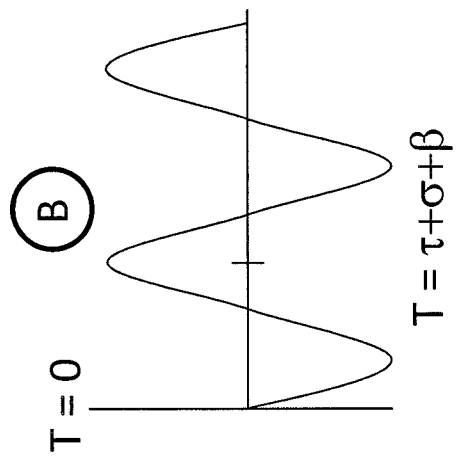
Figure 6C:
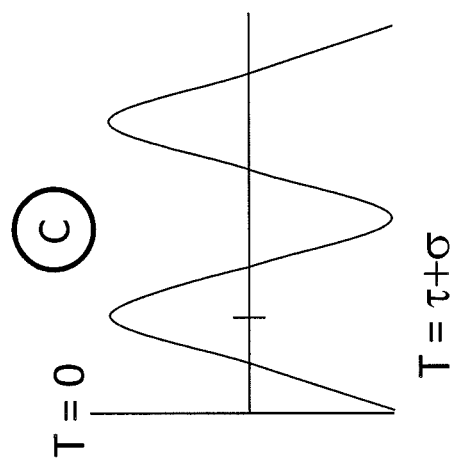
Figure 6B:
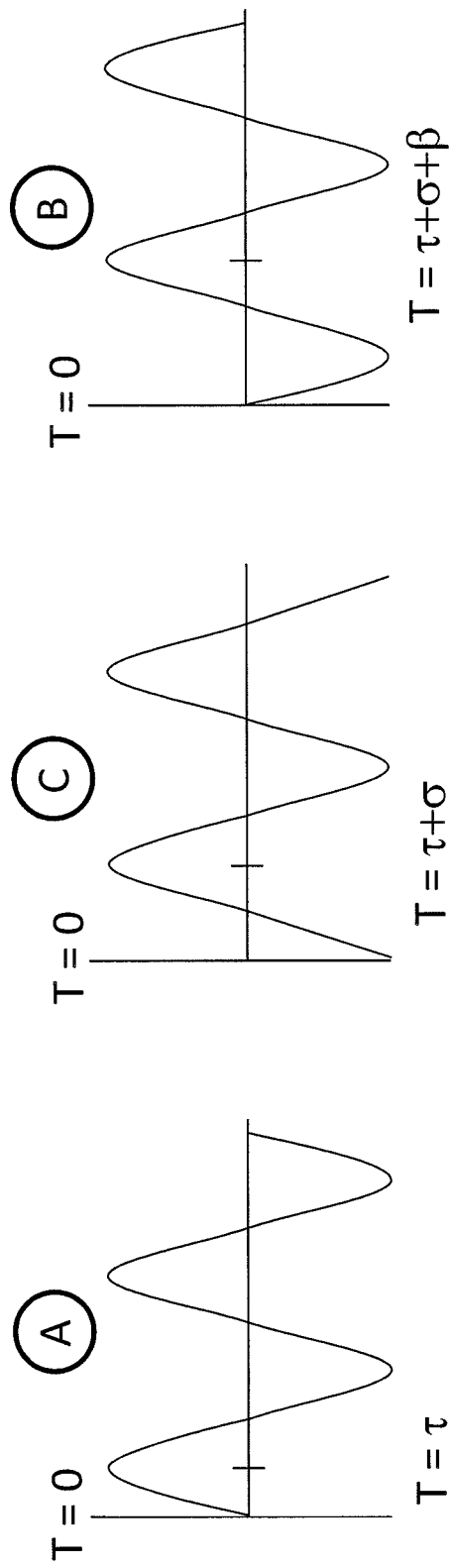

In FIG. 6, the blood flow 510 now originates from the left, as shown in FIG. 6A. Again, in this case we can set $\sigma=\beta$ because emitter C is located exactly between emitter A and emitter B relative to the incoming direction of the blood flow. However, it is important to notice that the phase differences of the emitter B and emitter C have been reversed, leaving emitter B as the trailing node that has the greatest phase difference ($\sigma+\beta$) from leading node emitter A. This is reflected in the waveforms shown in FIGS. 6B-6D. These two cases were chosen to illustrate how the phase differences change in direct relationship to changes in the incoming direction of flow. If the flow originated from the right side, one would redefine the leading node, record the new TDoA values, evaluate the phase relationship, and redefine the direction of flow relative to the arbitrary reference as described previously.

Other physiological parameters may be determined based on the same general principles. Because the nodes are a known distance apart, and because we are able to calculate the time difference of arrival between these nodes, the velocity of the pulsatile flow can also be calculated. Velocity definition requires a directional component which has been defined. Speed is defined as distance divided by time and can be calculated directly from the TDoA and known geometry of the array.

This method also provides input parameters for the calculation of PWV and PTT, which may be used to calculate blood pressure. Examples of empirically derived equations from literature are provided below:

$$BP_{PTT}=P1 \times PWV \times e^{(P3 \times PWV)}+P2 \times PWV^{P4}-(BP_{PTT,cal}-BP_{cal})$$

wherein $BP_{PTT}$=blood pressure derived from pulse transit time; $BP_{CAL}$=reference blood pressure; $BP_{PTT,CAL}$=calculated blood pressure corresponding to reference blood pressure; P1-P4=calibrated parameters from experimental reference data; and PWV=pulse wave velocity; and $$DPTT = \frac{L_f}{PWV} - \frac{L_e}{PWV} = (L_1 - L_2)\sqrt{\frac{\rho 2r}{E_0 e^{aP} h}} \tag{6}$$

wherein DPTT=difference in pulse transit time; $L_E$, $L_F$=pulse time arrival for case of finger and ear; $L_1$, $L_2$=pulse time arrival for any two distinct sites; p=density of blood; r=radius or vessel; $E_0$=elasticity of vessel wall; a=scaling parameter for vessel compliance; P=arterial blood pressure; and h=thickness of vessel wall.

Blood pressure may also be calculated by relating the pulse wave velocity or pulse transit time to the vessel wall elasticity. The Moens-Korteweg equation can be combined with the Hughes equation to give a value for arterial pressure:

$$P = \frac{1}{\varsigma}\ln\left(\frac{2R\rho c^2}{hE_o}\right)$$

wherein P=arterial blood pressure, $\zeta$=scaling parameter for vessel compliance; R=radius of vessel; $\rho$=density of blood; c=pulse wave speed; h=thickness of vessel wall; $E_0$=elasticity of vessel wall.

Any suitable method of calibration may be used. However, in some embodiments, calibration of the arterial pressure may be achieved by comparing the differences in the PTT under different hydrostatic pressures or in response to hypoxic or hyperoxic gases, by occlusion of site vasculature, or by comparison of PWV between resting and exercise states. Empirical data has shown strong correlation between variations in the PPG and blood pressure. The relationship between blood volume status, cardiac output, and vessel resistance allows for arterial blood pressure from the PPG signals. Normalizing these physiological factors and external variables such as temperature and pressure may provide even greater accuracy in non-invasive continuous blood pressure estimations.

Other PPG parameters may also be measured using known PPG techniques, including blood oxygen saturation, blood volume status and cardiac output status. For example, volumetric status may be calculated by area under the curve in relation to peak amplitude and base width of the pulsatile component of the PPG. Specific techniques include pattern recognition and adaptive algorithms to monitor changes in these parameters over time. Relative changes in volume can be monitored in real time. Calibration may also be useful, for example by infusion of a known volume of liquid, whereby comparing the wave shapes before and after infusion, we can quantify both blood volume and cardiac output in relation to the arterial blood pressure.

The PPG sensor arrays may also be used to determine respiration rate and/or other respiratory parameters and conditions, for example, as described in U.S. Publication No. 2008/0190430, filed Apr. 25, 2006, incorporated by reference herein in its entirety. As such, the PPG sensor may be used as a respiration detector in addition to a directional flow sensor. In some embodiments, the sensors described herein may be useful with a secondary respiration detector as well, either as part of the sensor or as a separate device, to monitor respiration in a patient. The data from two or more different respiration detectors may be compared, including in real time, which may provide additional information and/or enhanced confidence of the determination of respiratory parameters. As described elsewhere herein, secondary respiration detectors include, but are not limited to, thermistors, thermocouples, RTDs, moisture detectors, capnometers, microphones, pressure sensors, nasal airway flow detectors, such as nasal flow transducers, NAP, and via detectors of vibrations in the ear.

The sensors described herein may be used in combination with other physiological monitors as well, either as part of the sensor, if applicable, or as a separate device. Examples include oxygen sensors, pH sensors, blood pressure monitors, breath constituent monitors, blood constituent monitors, heart rate monitors (e.g., ECG) and depth of anesthesia monitors. The sensors described herein may also be used in combination with other PPG sensors, including those designed for emplacement at the nose (e.g., nasal alar, nasal septum and bridge of the nose), lip, cheek, tongue or a selected site at the ear (e.g., ear canal, concha, pinnae, scaphoid fossa, or ear lobe), forehead, fingers and toes. In some embodiments of the present invention, a sensor may be included in a system that provides feedback to medical personnel when generated when certain PPG signals or certain PPG signal levels are generated.

In some embodiments of the invention, provided are systems for monitoring a subject that include a PPG sensor according to an embodiment of the invention and a computer in communication with the PPG sensor. The computer is configured to process PPG signal streams from the sensor array to determine the direction of blood flow, blood velocity or other parameter described herein at a body site on which the PPG sensor is secured. The term "computer" refers to one or more signal processing devices, processors, processing modules and the like, and may include, but not limited to, microprocessors, microcontrollers, digital signal processors and the like, which may be coupled, for example with memory devices, including volatile and non-volatile memory devices. The systems may be used to perform the methods described herein, both those that relate to directional flow, velocity, PTT, PWV and/or BP calculations, but may also be used to monitor and/or analyze other physiological processes such as blood oxygen saturation, respiration, and the like.

There are many examples whereby the methods, devices and systems according to embodiments of the invention may be useful, including the non-limiting examples provided below.

Example 1: Evaluation of Skin Flaps

In some embodiments of the invention, the sensors, systems and methods described herein could also be used to evaluate the status of various skin flaps that are used to cover defects created during surgical procedures (e.g., head and neck cancers). Adequate blood perfusion is needed for the tissue to properly heal and survive. Pulse oximetry has been suggested as a means to determine the blood flow and viability of a flap by measuring oxygen saturation of the tissue. However, traditional pulse oximetry can only confirm blood is arriving to a site, whereas the present invention can more specifically determine where the blood supply is coming from and where it is going in order to determine if perfusion of the skin flap is viable or further intervention is needed.

For example, a sensor may be placed on or near a skin flap region, such as on the pedicle attaching blood vessels and nerves to the flap. If more than a single blood vessel perfuses the skin flap, changes in the direction of the blood flow between the two (or more) blood vessels could indicate an impending failure of adequate perfusion of the flap. If adequate perfusion is maintained, the flow will be from the direction of the donor site toward the flap. If the flow is reversed or diminished in one of the vessels, this could indicate that perfusion from that source has failed (e.g., the vessel has clotted) and immediate intervention would be needed to maintain the viability of the flap. By monitoring each vessel, it could be ascertained which vessel is clotted and/or the relative contribution of each vessel to the total flow.

Example 2—Evaluation of Cerebral Blood Flow

In some embodiments of the invention, the sensors, systems and methods described herein may be used to evaluate the adequacy of cerebral blood flow. The human nose is the only "external" organ (accessible non-invasively) supplied by two separate branches of the common carotid artery (a dual blood supply). The nose is supplied by the facial artery (a portion of the last branch of the external carotid artery) and the ophthalmic artery (originating from the first branch of the internal carotid artery). These arteries form a rich blood supply to the nose which is recognized to have multiple anastomoses between the facial and ophthalmic arteries on one side of the nose (intercarotid anastomoses) and also between these same vessels on the contralateral side of the nose (transfacial anastomoses). These vessels also form plexes on both the nasal septum and the lateral portions of the nose. This rich blood supply and the lack of intrinsic sympathetic innervation of the internal carotid branches provides adequate blood flow in almost all conditions including hypotension, hypoperfusion (e.g. vascular disease), hypothermia, anxiety (fight or flight response) and after delivery of medications that cause vasoconstriction. The ability to measure relative blood flow and direction of flow at the nose may provide a non-invasive means to monitor cerebral blood flow.

Areas where internal organs share dual blood supplies are often termed watershed areas. Internal organs watershed areas, despite a dual blood supply, are susceptible to infarction due to emboli or ischemia, particularly in watershed areas of the brain. The complications related to watershed areas in internal organs are not seen with the dual blood supply to the nose; thus the nose should not be considered a watershed area despite a dual blood supply. To the contrary, the dual blood supply guarantees adequate blood flow to the nose under a wide range of pathological conditions. It is not surprising that this is the case since the nose acts as a heat-moisture exchanger and the olfactory nerve ends on the nasal turbinates and nasal septum. Thus, adequate perfusion helps to prevent dehydration and for the sense of smell. For all intents and purposes, it can be assumed that inadequate perfusion of the nose parallels inadequate perfusion of the areas of the brain supplied by the internal carotid artery, and changes in blood flow patterns seen in vessels of the nose are indicative of similar changes in blood flow to the brain.

Recent studies have elucidated the blood supply to the nose more clearly than previously understood. Using Doppler ultrasound (DUS), Saban and colleagues (see Saban Y, et al., *Nasal Arterial Vasculature; Medical and Surgical Applications*, Arch. Facial Plast. Surg; 2012:429-36) showed that occlusion of the facial artery on one side leads to reversal of flow in the vessel distal to the point of occlusion indicating the flow is also supplied by the ophthalmic artery and that the dual blood supply guarantees adequate perfusion even if one vessel is occluded. Anatomical studies by the same authors demonstrate variable relative diameters of the facial and ophthalmic arteries among individuals but in all cases flow was maintained when one or the other arteries were occluded. Further, if both arteries are occluded on one side, flow is still present due to transfacial anastomoses from the contralateral side (this was demonstrated in approximately 50% of studies, but the authors believe this was due to technical issues, not the absence of transfacial anastomoses). While DUS is helpful in demonstrating the rich anastomoses that occur in the nasal arterial bed, it is impractical for continuous monitoring of the relative contribution of blood supply from the vessels supplying the nose. The contour and direction of the velocity profile is quite different for the facial and ophthalmic arteries with the facial arteries demonstrating a high resistance index and the ophthalmic artery demonstrating a low resistance index. Thus, in some embodiments, the contribution of blood flow from the internal carotid artery could be continuously evaluated by monitoring blood direction, PPG contour and amplitude and velocity at the nose.

Patients presenting to the hospital with significant closed-head injuries are at great risk of developing increased intracranial pressure (ICP) which may result in decrease intracranial (cerebral) blood flow and, if untreated, death. The instant invention could be used to evaluate whether cerebral blood flow is adequate or inadequate without the need for surgical intervention. In one embodiment, the sensor could be placed, for example, either on one or both nasal alae, upon presentation to the Emergency Department or even during transport to the hospital or at the scene upon arrival of emergency medical personnel. Initially, before the development of increased ICP, the contribution of blood flow from the internal carotid and external carotid arteries would be evaluated by the contour and direction of the PPG signal. Normally, since the external carotid artery (ECA) contribution produces a contour typical of a high resistive index circuit which is "peaked" with rapid "run-off" the direction of flow in most locations on the nose favors ECA blood flow. By contrast, the internal carotid artery (ICA) contour is blunted with slower "run-off" and the direction of ICA flow is overshadowed by the predominant flow of the ECA. It is important to point out that the direction of flow is site dependent on the nose and that there are regions that are anatomically closer to the ophthalmic artery where the direction of flow would reflect ICA blood flow. Further, if ICP has already developed at the time of placement of the sensor array, the contour would be indicative of increased ICP.

Thus, at any particular time, the integrated contour of the PPG signal is indicative of the relative contribution of the ECA and ICA to total blood flow and direction of flow in the region of the sensor. Depending on where the sensor is placed, the direction of flow would be predominantly from the ICA or ECA. Therefore, improvements in ICP would show a contour indicative of more blood flow from the ICA and the direction of flow as evaluated by the contour of the PPG waveform would likewise indicate improved flow from the ICA. Should intracranial pressure increase, there will be a diminution of the ICA component of the PPG signal and the predominant signal would be indicative of only ECA blood flow and the direction of the flow would indicate a preponderance of ECA flow. Techniques that decrease ICP such as medications and hyperventilation should return the contour of the PPG signal to that when the ICP was normal.

Recent PPG studies performed by the inventors evaluated the effects of compression of the facial artery, the ophthalmic artery, or both on blood flow to the nasal alae on both the side of compression and the contralateral side during DUS. In general, compression of the facial artery leads to a reversal of flow in the blood vessel (angular artery) in the groove alongside the nose where the facial and ophthalmic arteries anastomose indicating an increased contribution from the ophthalmic artery during facial artery compression and a predominance of facial artery flow in the majority of people. Compression of the facial artery leads to no or a modest decrease in ipsilateral alar blood flow as measured by PPG in most individuals, although one individual had a drop of 70% probably indicative significant preexisting vascular disease, and no decrease in blood flow to the contralateral ala.

Compression of the ophthalmic artery caused a small decrease in blood flow to the angular artery and resulted in either no decrease or only a small decrease in the ipsilateral alar PPG signal and no change in the contralateral alar blood flow. Compression of both the facial and ophthalmic arteries leads to a variable decrease in ipsilateral angular artery blood flow but again either no or modest decrease in blood flow to the ipsilateral ala was seen, indicating compensatory blood flow from the contralateral arteries. Thus the PPG signal is robust and reliable even with compromised blood flow on one side and can be measured on a continuous basis. Therefore, relative changes in the PPG signal (e.g., contour and amplitude) (ideally measured on both alae) and direction of blood flow can be used to determine whether there is a significant decrease in intracerebral blood flow (e.g., increased ICP) either regionally (one hemisphere) or globally and whether increased ICP is responsive to therapeutic intervention.

Example 3: Laminar or Turbulent Flow in an Artery

In some embodiments of the invention, the sensors, systems and methods described herein are used to determine whether there is laminar or turbulent flow in an artery. Laminar flow may indicate a lack of atherosclerosis, while turbulent flow may indicate its presence. The instant invention by means described below could be used to detect the type of flow pattern using either transmission or reflectance PPG and can be used to evaluate peripheral (superficial arteries) such as the brachial, carotid, femoral and others for turbulence before and after surgical procedures and to evaluate the patency of shunts such as shunts placed in the arms for renal dialysis and implanted shunts along segments of arteries such as for aneurysms particularly of the aorta. The directional blood flow sensors and methods described herein may be used to determine from which direction the blood is flowing, and the laminar blood flow may alter the phase differences in different ways than the turbulent blood flow because there will not be the same phase shift in the waveforms. Laminar flow will produce a strong directional component that can be analyzed with statistical methods such as signal to noise ratio. When the flow is turbulent, the signal to noise ratio of the directional component will degrade. The turbulence in blood flow may be monitored over time to assess whether turbulence is increasing, decreasing remaining constant.

Example 4: Pulmonary Artery Banding

In some embodiments of the invention, the sensors, systems and methods described herein are used during surgical procedures to evaluate the direction and quality of blood flow in a single vessel. For instance, during a number of procedures for congenital heart disease, the surgeon must "band" an artery, usually the pulmonary artery, to reduce the amount of blood being shunted into the right ventricle (left to right shunt).

"Pulmonary artery banding (PAB) is a technique of palliative surgical therapy used by congenital heart surgeons as a staged approach to operative correction of congenital heart defects. This technique was widely used in the past as an initial surgical intervention for infants born with cardiac defects characterized by left-to-right shunting and pulmonary overcirculation. The primary objective of performing pulmonary artery banding is to reduce excessive pulmonary blood flow and protect the pulmonary vasculature from hypertrophy and irreversible (fixed) pulmonary hypertension. More recently, pulmonary artery banding has played a role in the preparation and "training" of the left ventricle (LV) in patients with D-transposition of the great arteries (d-TGA) who are evaluated for a delayed arterial switch procedure. It has found a similar role in training the LV in patients with L-transposition of the great arteries (L-TGA) who may also be candidates for an arterial switch procedure." (Pulmonary Artery Banding, Shabir Bhimji, M D, PhD; Chief Editor: John Kupferschmid, M D). During banding, the surgeon must estimate how much flow is decreased to the pulmonary artery and how much blood is increased in the aorta. The instant technology could remain in place throughout the surgical procedure and guide the surgeon in achieving the proper balance of flow to the pulmonary artery and aorta, which should be essentially equal in magnitude.

For example, the sensors of the instant invention could be placed on the pulmonary artery and the aorta. Initially, blood flow to the pulmonary artery would be far greater than flow to the aorta. The surgeon would be guided on how much to reduce the lumen of the pulmonary artery and thus increase the flow to the aorta until the flows were matched. An example of where the direction of flow would be particularly important to monitor would be if there is a patent ductus arteriosus alone or in combination with other cardiac lesions. The surgeon can use the instant invention to determine when flow in the ductus is reversed, indicating that flow is now going in the proper direction rather than back to the right ventricle and pulmonary vasculature. Often drugs are used to close the patent ductus and the instant sensor could tell when flow ceases through the ductus or reverses direction, reducing the blood flow to the lungs in favor of the systemic circulation.

In the drawings and specification, there have been disclosed embodiments of the invention and, although specific terms are employed, they are used in a generic and descriptive sense only and not for purposes of limitation, the scope of the invention being set forth in the following claims.

We claim:
1. A system for monitoring a subject, comprising:
 a photoplethysmograph (PPG) sensor comprising (a) an array that comprises at least three emitters and at least one detector, (b) an array that comprises at least three detectors and at least one emitter, or (c) both; and
 a computer in communication with the PPG sensor, wherein the computer uses (a) a geometry of the emitters, the detectors, or both, and (b) at least one of Time Difference of Arrival and Angle of Arrival to determine direction of blood flow at a body site on which the PPG sensor is secured; wherein Time Difference of Arrival is determined based on a difference between at least one of: peak events between nodes, zero crossing events between nodes, and phase difference between at least two of the PPG signal streams from at least two of the emitters; and wherein Angle of Arrival is determined based on at least one of: peak events between nodes, zero crossing events between nodes, and phase difference between at least two of the PPG signal streams from at least two of the emitters.

2. The system of claim 1, wherein the PPG sensor comprises the array of at least three emitters and at least one detector, and wherein the phase difference used to determine at least one of: Time Difference of Arrival and Angle of Arrival is a phase difference between at least three PPG signal streams from the at least three emitters.

3. The system of claim 1, wherein the PPG sensor comprises the array of at least three detectors and at least one emitter, wherein the phase difference used to determine at least one of: Time Difference of Arrival and Angle of Arrival is a phase difference detected by the at least three detectors from at least one PPG signal stream generated by the at least one emitter.

4. The system of claim 1, wherein the array of at least three emitters, the array of at least three detectors, or both is a linear array.

5. The system of claim 1, wherein the array of at least three emitters, the array of at least three detectors, or both is a 2D array.

6. The system of claim 1, wherein the computer further determines at least one of pulse transit time (PTT) and pulse wave velocity (PWV) from at least one PPG signal stream from the PPG sensor.

7. The system of claim 1, wherein the computer further determines the blood pressure from at least one PPG signal stream from the PPG sensor.

8. A method for monitoring a subject comprising:
receiving PPG signal streams from a PPG sensor, wherein the PPG sensor comprises (a) an array that comprises at least three emitters and at least one detector, (b) an array that comprises at least three detectors and at least one emitter, or (c) both;
determining a Time Difference of Arrival based on a difference between at least one of: peak events between nodes, zero crossing events between notes, and a phase difference between at least two of the PPG signal streams from at least two of the emitters;
determining an Angle of Arrival based on at least one of: peak events between nodes, zero crossing events between nodes, and a phase difference between at least two of the PPG signal streams from at least two of the emitters; and
determining a direction of blood flow at a site on which the PPG sensor is secured based on (a) a geometry of the emitters, the detectors, or both, and (b) at least one of Time Difference of Arrival and Angle of Arrival.

9. The method of claim 8, wherein the phase difference used to determine at least one of: Time Difference of Arrival and Angle of Arrival is a phase difference between at least three PPG signal streams from the at least three emitters.

10. The method of claim 8, wherein the phase difference phase difference used to determine at least one of: Time Difference of Arrival and Angle of Arrival is detected by the at least three detectors from at least one PPG signal stream generated by the at least one emitter.

11. The method of claim 8, wherein the array of at least three emitters, the array of at least three detectors, or both is a linear array.

12. The method of claim 8, wherein the array of at least three emitters, the array of at least three detectors, or both is a 2D array.

13. The method of claim 8, further comprising:
determining at least one of pulse transit time (PTT) and pulse wave velocity (PWV) from at least one PPG signal stream from the PPG sensor.

14. The method of claim 8, further comprising:
determining the blood pressure from at least one PPG signal stream from the PPG sensor.

\* \* \* \* \*